(12) United States Patent
Brugere et al.

(10) Patent No.: US 10,238,695 B2
(45) Date of Patent: Mar. 26, 2019

(54) USE OF MICROORGANISMS FOR REDUCING THE LEVEL OF TRIMETHYLAMINE IN A HUMAN BODY CAVITY, IN PARTICULAR FOR THE TREATMENT OF TRIMETHYLAMINURIA OR OF BACTERIAL VAGINOSIS AND THE PREVENTION OF CARDIOVASCULAR DISEASES

(71) Applicant: UNIVERSITE D'AUVERGNE CLERMONT I, Clermont Ferrand (FR)

(72) Inventors: Jean-François Brugere, Issoire (FR); Guillaume Borrel, Gieres (FR); Paul William O'Toole, Mallow Co Cork (IR); Corinne Malpuech-Brugere, Issoire (FR); Monique Alric, Saint Flour l'Etang (FR)

(73) Assignee: UNIVERSITE D'AUVERGNE CLERMONT I, Clermont Ferrand (FR)

( * ) Notice: Subject to any disclaimer, the term of this patent is extended or adjusted under 35 U.S.C. 154(b) by 0 days.

(21) Appl. No.: 14/648,186

(22) PCT Filed: Sep. 27, 2013

(86) PCT No.: PCT/EP2013/070249
§ 371 (c)(1),
(2) Date: May 28, 2015

(87) PCT Pub. No.: WO2014/082773
PCT Pub. Date: Jun. 5, 2014

(65) Prior Publication Data
US 2016/0074440 A1 Mar. 17, 2016

(30) Foreign Application Priority Data

Nov. 30, 2012 (FR) ...................................... 12 61507
Mar. 13, 2013 (FR) ...................................... 13 52239
Jul. 15, 2013 (FR) ...................................... 13 56937

(51) Int. Cl.
*A61K 35/74* (2015.01)
*C12N 9/10* (2006.01)
*A61K 38/45* (2006.01)

(52) U.S. Cl.
CPC .............. *A61K 35/74* (2013.01); *A61K 38/45* (2013.01); *C12N 9/1007* (2013.01); *C12Y 201/0125* (2015.07); *Y02A 50/473* (2018.01)

(58) Field of Classification Search
None
See application file for complete search history.

(56) References Cited

U.S. PATENT DOCUMENTS 9,168,233 B2  10/2015  Hazen et al.
9,694,020 B2   7/2017  Hazen 2011/0280835 A1*  11/2011  March ................ C07K 14/4705
                                               424/93.2
2012/0157397 A1*   6/2012  Hazen .................... C12Q 1/025
                                                  514/39
2013/0345171 A1   12/2013  Hazen et al.
2016/0089386 A1    3/2016  Hazen
2016/0089387 A1    3/2016  Hazen
2016/0101062 A1    4/2016  Hazen et al.

FOREIGN PATENT DOCUMENTS

CN       102458481        5/2012
WO    WO-92/20789       11/1992
WO   WO 9951753 A1 *  10/1999  .......... C07K 14/245
WO    WO-02/061425      8/2002
WO   WO-2010/138899    12/2010

OTHER PUBLICATIONS

Genbank Accession No. AGI85869.1.*
Fog Bentzon et al. Mechanisms of Plaque Formation and Rupture. Circulation Research, 2014. 114:1852-1866.*
Sakakura et al. Pathophysiology of Atherosclerosis Plaque Progression. Heart, Lung and Circulation, 2013. 22:399-411.*
Jia et al. Gut Microbiotia: A potential New Territory for Drug Targeting. Nature Reviews, 2008. 7:123-129.*
Chin et al. In sight of current technologies for Oral Delivery of Proteins and peptides Drug Discovery Today: Technologies, 2012: 9(2) e105-112.*
Paul et al (The Trimethylamine Methyltransferase Gene and Multiple Dimethylamine Methyltransferase Genes of Methanosarcina barkeri Contain In-Frame and Read-Through Amber Codons. Journal of Bacteriology, 2000. 2520-2529.*
GenBank Accession No. NZ_CAJE01000023.*
Genbank Accession No. NZ_CAJE01000013.*
Begley et al. Bile Sale Hydrolase Activity in Probiotics. Applied and Environmental Microbiology, 2006. 1729-1738.*
Krzycki, Joseph A. The Direct Genetic Encoding of Pyrrolysine. Current Opinion in Microbiology, 2005. 8:706-712.*
Wang, et al., "Gut flora metabolism of phosphatidylcholine promotes cardiovascular disease", Apr. 7, 2011, pp. 57-63, vol. 472, No. 7341, Nature.

(Continued)

Primary Examiner — Christopher M Babic
Assistant Examiner — Kimberly A. Aron
(74) Attorney, Agent, or Firm — B. Aaron Schulman, Esq.; Stites & Harbison, PLLC

(57) ABSTRACT

Composition containing a microorganism, preferably an Archaea, expressing a TMA methyltransferase and a TMA methyl group acceptor corrinoid protein, capable of metabolizing trimethylamine (TMA) in the presence of hydrogen in a human cavity, such as the intestine or the vagina, for use as a medicament for treating, reducing or eliminating TMA at the level of the human cavity. In addition, a composition containing a TMA methyltransferase and a TMA methyl group acceptor corrinoid protein. These compositions are of use for treating trimethylaminuria, for treating vaginal fluids in the case of bacterial vaginosis and for reducing or eliminating odours due to TMA. These compositions are also of use for reducing the level of plasma TMAO, for preventing the formation of atheroma plaques and/or for preventing cardiovascular diseases.

10 Claims, No Drawings
Specification includes a Sequence Listing.

(56) References Cited

OTHER PUBLICATIONS

Koeth, et al., "Intestinal microbiota metabolism of L-carnitine, a nutrient in red meat, promotes atherosclerosis", Apr. 7, 2013, pp. 1-11, nature medicine.
International Serach Report dated Nov. 21, 2013 in PCT/EP2013/070249.
Chalmers, et al., "Diagnosis and management of trimethylaminuria (FM03 deficiency) in children", Feb. 1, 2006, pp. 162-172, vol. 29, No. 1, Journal of Inherited Metabolic Disease, Kluwer Academic Publishers, DO.
Dridi, et al., "Archaea as emerging organisms in complex human microbiomes", Mar. 8, 2011, pp. 56-63, vol. 36, No. 3, Anaerobe, XP028094572.
Mastromarino, et al., "Bacterial vaginosis: a review on clinical trials with probiotics", Jul. 1, 2013, pp. 229-238, vol. 36, No. 3, New Microbiologica, XP009172723.
Vujic, et al, "Efficacy of orally applied probiotic capsules for bacterial vaginosis and other vaginal infections: a double-blind, randomized, placebo-controlled study", May 1, 2013, pp. 75-79, vol. 168, No. 1, European Journal of Obstetrics & Gynecology and Reproductivebiology, Excerpta Medica, Amsterdam, NL, XP009172718.
Rak, et al., "The diet-microbe morbid union", Apr. 7, 2011, pp. 40-41, vol. 472, News & Views, Cardiovascular Disease.
Dridi, et al, "Age-related prevalence of *Methanomassiliicoccus luminyensis* in the human gut microbiome", 2012, pp. 1-5, Human Intestinal Archaea.
Wolrath, et al., "Trimethylamine and trimethylamine oxide levels in normal women and women with bacterial vaginosis reflect a local metabolism in vaginal secretion as compared to urine", 2005, pp. 513-516, vol. 113, APMIS.
Wolrath, et al, "Trimethylamine content in vaginal secretion and its relation to bacterial vaginosis", 2002, pp. 819-824, vol. 110, APMIS.
Gorlas, et al, "Complete Genome Sequence of *Methanomassiliicoccus luminyensis*, the Largest Genome of a Human-Associated Archea Species", Sep. 2012, pp. 4745, vol. 194, No. 17, Journal of Bacteriology.
Dridi, et al., "*Methanomassiliicoccus luminyensis* gen. nov., sp. no., a methanogenic archeaeon isolated from human feaces", 2012, pp. 1902-1907, vol. 62, International Journal of Systematic and Evolutionary Microbiology.
Ferguson, et al., "RamA, a Protein Required for Reductive Activation of Corrinoid-dependent Methylamine Methyltransferase Reactions in Methanogenic Archaea", Jan. 23, 2009, pp. 2285-2295, vol. 284, No. 4, The Journal of Biological Chemistry.
Vujic, et al., "Efficacy of orally applied probiotic capsules for bacterial vaginosis and other vaginal infections: a double-blind, randomized, placebo-controlled study", 2013, pp. 75-79, vol. 168, European Journal of Obstetrics Gynecology and Reproductive Biology.
Morgavi, et al., "Rumen microbial communities influence metabolic phenotypes in lambs", Oct. 2015, pp. 1-13, vol. 6, Frontiers in Microbiology.
Brugere, et al., "Archaebiotics", Oct. 14, 2016, pp. 5-10, vol. 5, No. 1, Gut Microbes.

\* cited by examiner

USE OF MICROORGANISMS FOR REDUCING THE LEVEL OF TRIMETHYLAMINE IN A HUMAN BODY CAVITY, IN PARTICULAR FOR THE TREATMENT OF TRIMETHYLAMINURIA OR OF BACTERIAL VAGINOSIS AND THE PREVENTION OF CARDIOVASCULAR DISEASES

STATEMENT REGARDING SEQUENCE LISTING

The Sequence Listing associated with this application is provided in text format in lieu of a paper copy, and is hereby incorporated by reference into the specification. The name of the text file containing the Sequence Listing is "P11311US00SeqListing revised110215.txt." The size of the text file is 2.09MB (2,195,578 bytes), it was created on Nov. 2, 2015, and is being submitted electronically via EFS-Web.

The present invention relates to the use of microorganisms allowing metabolism of trimethylamine (TMA) in at least one human body cavity ("human cavity" hereafter) comprising microbial flora able to produce TMA and therefore reducing the level of this TMA at the human cavity.

The invention relates to the use of these microorganisms in the intestine in order to reduce the intestinal level of this TMA. The goal of the invention is notably to allow treatment of trimethylaminuria and/or reduce the trimethylamine N-oxide (TMAO) level, which gives the possibility of preventing the formation of atheromatous plaques and of providing an additional means for preventing cardiovascular diseases.

The invention also relates to the delivery in situ of enzymes allowing metabolism of TMA.

Trimethylaminuria (or TMAU, a uremia with TMA, or fish-odor syndrome) is a genetic disease in which a person genetically deficient in an enzyme (flavine containing monooxygenase 3 FMO3) cannot effectively transform TMA into TMAO at the liver. Also in certain cases, the deficiency in this capability of transformation is sporadic and acquired. Trimethylamine then accumulates in the body and is finally removed through sweat, urine and exhalation, with a strong fish smell. If no actual study shows the general incidence of the disease, the figure of 1% of the American population has however been put forward. In the following, such a person will be designated as a TMA-metabolism deficient patient.

Intestinal TMA has a food origin and notably results from the conversion of TMAO, choline or lecithin brought by food (notably eggs, meat, liver, wheat germ, fish, etc.). These compounds are transformed at the intestine by intestinal microbiota.

Moreover, in persons having the active FMO3 enzyme, the TMA is transformed into TMAO in the liver and this metabolite is again found in the blood flow. Wang et al. (Nature 2011, 472 (7341), 57-63; see also K Rak and D J Rader, Cardiovascular Disease, News and Views, Nature 2011, 472, 40-41) teach that circulating TMAOs may contribute to the development of atheromatous plaques in the arteries and therefore to heart diseases.

Bacterial vaginosis is a benign disease in women, the cause of which is an imbalance of the vaginal microbial flora. This imbalance would stem from depletion of lactobacillar flora in favor of increase in an anaerobic flora notably comprising *Gardnerella vaginalis*. Bacterial vaginosis is characterized by greyish and fragrant vaginal losses or fluids. The smell of these vaginal losses or fluids is due to the presence of TMA (Wolrath et al. APMIS 2002, 110, 819-824; also see Wolrath et al. APMIS 2005, 113, 513-516).

The invention also relates to the use of these microorganisms in the vagina in order to reduce the level of TMA in vaginal fluids. The object of the invention is notably to allow treatment of vaginal fluids in the case of bacterial vaginosis or of any disorder or disease causing a local production of TMA, which gives the possibility of reducing the strong smells of vaginal losses or vaginal fluids.

The object of the invention is also a novel microorganism which may be used in these applications.

Methanogenic Archaea are microorganisms which produce methane under anaerobic conditions. Certain Archaea are found in the digestive system of animals such as ruminants, as well as in certain human individuals, in particular elderly individuals.

Thus, the team of B. Dridi (International Journal of Systematic Evolutionary Microbiology 2012, 62, 1902-1907) presents the isolation of such a microorganism with the name of Methanomassiliicoccus luminyensis for which it is described that under an atmosphere with $H_2$, this Archaea may reduce methanol to methane. It is also described that this microorganism is incapable of methanogenesis from trimethylamine, as well as from other substrates, under a $CO_2$ atmosphere. The complete genome of this Archaea was published and mentioned in A. Gorlas, Journal of Bacteriology, September 2012, Vol. 194, 17, p. 4745, the genome being accessible in GenBank under the access references CAJE01000001 to CAJE01000026.

At the present time, notably in humans, no microorganisms, notably Archaea, have been described as able to use and metabolize TMA in vivo.

The inventors managed to identify a novel species of methanogenic Archaea in a sample of salts from a human individual, a species comprising a gene coding for a TMA methyltransferase (gene mttB) and a gene coding for a corrinoid protein accepting a methyl group from TMA (gene mttC), capable, in the presence of hydrogen and under anaerobic conditions encountered in certain organs or cavities which they delimit, such as the intestine, the human colon or the vagina, of metabolizing TMA, so that the proposal here is to use these microorganisms for metabolizing TMA for reducing its level, notably the intestinal or vaginal level. It was further discovered that this strain of Archaea also has a gene of resistance to biliary salts, notably a gene coding for hydrolysis of biliary salts, thereby promoting survival and maintaining of the microorganism at the intestine level. This microorganism is designated hereafter as strain 1 or Methanomethylophilus alvus. The inventors have also identified that the strain of Archaea Methanomassiliicoccus luminyensis described by D. Didri et al. (supra), sometimes designated hereafter strain 2, also has genes coding for TMA methyltransferase and for a corrinoid protein accepting a methyl group from TMA able to allow metabolism of TMA in the presence of hydrogen in the intestine. It is believed that TMA is metabolized with formation of methylated proteins (methylated corrinoid proteins) which capture the methyls of TMA. This methylated protein is then no doubt driven into the route of methanogenesis, resulting in the production of methane.

By definition, one will equally refer here to an organ delimiting a cavity or to the cavity itself, which may contain anaerobic microbial flora able to produce or producing TMA. It is also possible to define this organ or cavity as an organ or cavity containing TMA produced by microbial flora. This TMA production is generally obtained in the presence of a hydrogen source stemming from microbial metabolism.

The object of the invention is therefore a composition containing a microorganism expressing a TMA methyltransferase. The microorganism is capable of metabolizing trimethylamine (TMA) in the presence of hydrogen in a human organ or cavity according to the definition supra. The composition may be used as a drug for treating, reducing or suppressing TMA at the human organ or cavity, and/or treating any pathology, inconvenience or disorder characterized by the presence of TMA or derived from the presence of TMA.

A composition according to the invention contains a microorganism expressing TMA methyltransferase, capable of metabolizing trimethylamine (TMA) in the presence of hydrogen in at least one human cavity comprising microbial flora able to produce TMA, for use as a drug for treating, reducing or suppressing TMA at the human cavity.

According to a first aspect, the invention relates to a composition containing a microorganism expressing a TMA methyltransferase, capable of metabolizing trimethylamine (TMA) in the presence of hydrogen in the intestine, for use as a drug for reducing or suppressing TMA at the intestine level and/or in the liver.

More specifically, in a first embodiment, the use aims at treating trimethylaminuria. The treated patient has a deficiency in the capacity of metabolizing TMA. Notably, he/she is deficient in an active FMO3 enzyme.

In a second embodiment, the use aims at reducing the hepatic metabolite level of TMA, TMAO, notably plasma TMAO. This use may aim at preventing the formation of atheromatous plaques and/or preventing cardiovascular diseases. The targeted patient is either a patient capable of metabolizing TMA, or a patient with TMA-metabolism deficiency but treated with a drug allowing reestablishment of TMA metabolism into TMAO. The metabolization of TMA upstream, for example with the composition according to the invention, then allows limitation of the production of TMAO by the liver.

The use of the composition according to the invention in a TMA-metabolism deficient patient gives the possibility of combining both effects, metabolism of TMA or treatment of trimethylaminuria and reduction of plasma TMAO, prevention of the formation of atheromatous plaques and/or prevention of cardiovascular diseases.

The object of the invention is also a composition containing a microorganism expressing TMA methyltransferase, capable of metabolizing trimethylamine (TMA) in the presence of hydrogen in the intestine, for treating trimethylaminuria.

The object of the invention is therefore also a composition containing a microorganism expressing a TMA methyltransferase, capable of metabolizing trimethylamine (TMA) in the presence of hydrogen in the intestine, for use as a drug for reducing the plasma TMAO level, preventing the formation of atheromatous plaques and/or preventing cardiovascular diseases.

According to a second aspect, the invention relates to a composition containing a microorganism expressing TMA methyltransferase, capable of metabolizing trimethylamine (TMA) in the presence of hydrogen in the vagina, in order to treat, reduce or suppress the TMA present in the vagina or the vaginal fluids.

In particular, without intending to be bound by theory, it is believed that TMA present in the vagina or the vaginal fluids results from the conversion of compounds, comprising a nitrogen-containing group substituted with three methyls, by the vaginal microbial flora.

In an embodiment, the use aims at treating vaginal fluids in the case of bacterial vaginosis and at reducing or suppressing the smells due to the presence of TMA.

In order to ensure metabolization of TMA by the microorganisms according to the invention, it is preferable that the methyls of the TMA be transferred to another molecule.

In an embodiment, the microorganism also expresses a corrinoid protein able to play this role of methyl acceptor. This protein is in particular a corrinoid protein accepting a methyl group from TMA.

In an embodiment, the composition comprises a microorganism comprising the gene coding for a TMA methyltransferase having the sequence SEQ ID NO: 1 or 2, or an equivalent sequence (of a methyltransferase active on TMA) having more than 90% of identity, notably having 90, 91, 92, 93, 94, 95, 96, 97, 98 or 99% of identity, with SEQ ID NO: 1 or 2.

In an embodiment, the composition comprises a microorganism comprising the gene coding for a TMA methyltransferase, this gene having the sequence SEQ ID NO: 3 or 4, or an equivalent sequence (sequence coding for a methyltransferase active on TMA) having more than 90% of identity, notably having 90, 91, 92, 93, 94, 95, 96, 97, 98 or 99% of identity, with SEQ ID NO: 3 or 4.

In an embodiment, the composition comprises a microorganism comprising the gene coding for a corrinoid protein accepting a methyl group from TMA, having the sequence SEQ ID NO: 5 or 6, or an equivalent sequence (of a corrinoid protein accepting a methyl group capable of capturing the methyls of TMA in the presence of a methyltransferase) having more than 90% of identity, notably having 90, 91, 92, 93, 94, 95, 96, 97, 98 or 99% of identity, with SEQ ID NO: 5 or 6.

In an embodiment, the composition comprises a microorganism comprising the gene coding for a corrinoid protein accepting a methyl group from TMA, this gene having the sequence SEQ ID NO: 7 or 8, or an equivalent sequence (sequence coding for a corrinoid protein accepting a methyl group capable of capturing the methyls of TMA in the presence of a methyltransferase) having more than 90% of identity, notably having 90, 91, 92, 93, 94, 95, 96, 97, 98 or 99% of identity, with SEQ ID NO: 7 or 8.

In an embodiment, the composition comprises a microorganism comprising the gene coding for a TMA methyltransferase having the sequence SEQ ID NO: 1, or an equivalent sequence as defined supra, and the gene coding for a corrinoid protein accepting a methyl group from TMA, having the sequence SEQ ID NO: 5, or an equivalent sequence as defined supra.

In an embodiment, the composition comprises a microorganism comprising the gene coding for a TMA methyltransferase having the sequence SEQ ID NO: 2, or an equivalent sequence as defined supra, and the gene coding for a corrinoid protein accepting a methyl group from TMA, having the sequence SEQ ID NO: 6, or an equivalent sequence as defined supra.

In an embodiment, the composition comprises a microorganism comprising the gene coding for a TMA methyltransferase, this gene having the sequence SEQ ID NO: 3, or an equivalent sequence as defined supra, and the gene coding for a corrinoid protein accepting a methyl group from TMA, this gene having the sequence SEQ ID NO: 7, or an equivalent sequence as defined supra.

In an embodiment, the composition comprises a microorganism comprising the gene coding for a TMA methyltransferase, this gene having the sequence SEQ ID NO: 4, or an equivalent sequence as defined supra, and the gene coding for a corrinoid protein accepting a methyl group from TMA, this gene having the sequence SEQ ID NO: 8, or an equivalent sequence as defined supra.

In an embodiment, the microorganism also includes a gene for resistance to biliary salts, preferably a gene coding for a hydrolase of biliary salts, such as choloylglycine hydrolase.

In an embodiment, the choloylglycine hydrolase has the sequence SEQ ID NO: 9, or an equivalent sequence (of an hydrolase active on biliary salts) having more than 90% of identity, notably having 90, 91, 92, 93, 94, 95, 96, 97, 98 or 99% of identity, with SEQ ID NO: 9. In an embodiment, the choloylglycine hydrolase is coded by a gene having the sequence SEQ ID NO: 10, or an equivalent sequence (sequence coding for an hydrolase active on biliary salts) having more than 90% of identity, notably having 90, 91, 92, 93, 94, 95, 96, 97, 98 or 99% of identity, with SEQ ID NO: 10.

In an embodiment, the composition comprises a microorganism comprising the gene coding for a TMA methyltransferase having the sequence SEQ ID NO: 1, or an equivalent sequence as defined supra, the gene coding for a corrinoid protein accepting a methyl group from TMA having the sequence SEQ ID NO: 5, or an equivalent sequence as defined supra, and the gene coding for a choloylglycine hydrolase having the sequence SEQ ID NO: 9, or an equivalent sequence as defined supra.

In an embodiment, the composition comprises a microorganism comprising the gene coding for a TMA methyltransferase, this gene having the sequence SEQ ID NO: 3, or an equivalent sequence as defined supra, the gene coding for a corrinoid protein accepting a methyl group from TMA, this gene having the sequence SEQ ID NO: 7, or an equivalent sequence as defined supra, and the gene coding for a choloylglycine hydrolase, this gene having the sequence SEQ ID NO: 10, or an equivalent sequence as defined supra.

According to a preferred embodiment, in these compositions, the microorganism is a methanogenic Archaea, notably of human or animal origin, preferably human origin.

In an embodiment, the microorganism is a methanogenic Archaea for which the RNA 16S is coded by the DNA sequence SEQ ID NO: 11 (strain 1 identified by the inventors) or a sequence having more than 85%, notably more than 90% of identity, notably having 90, 91, 92, 93, 94, 95, 96, 97, 98 or 99% of identity, with SEQ ID NO. 11. This microorganism comprises the gene coding for a TMA methyltransferase having the sequence SEQ ID NO: 1, or an equivalent sequence as defined supra, the gene coding for a corrinoid protein accepting a methyl group from TMA, having the sequence SEQ ID NO: 5, or an equivalent sequence as defined supra, and the gene coding for a choloylglycine hydrolase, having the sequence SEQ ID NO: 9, or an equivalent sequence as defined supra. This microorganism comprises the gene coding for a TMA methyltransferase, this gene having the sequence SEQ ID NO: 3, or an equivalent sequence as defined supra, the gene coding for a corrinoid protein accepting a methyl group from TMA, this gene having the sequence SEQ ID NO: 7, or an equivalent sequence as defined supra, and the gene coding for a choloylglycine hydrolase, this gene having the sequence SEQ ID NO: 10, or an equivalent sequence as defined supra. The genome of this strain, designated here as Methanomethylophilus alvus, is shown in SEQ ID NO: 13.

In an embodiment, the microorganism is a methanogenic Archaea for which the RNA 16S is coded by the DNA sequence SEQ ID NO: 12 (strain 2 described by Dridi supra, strain DSM No. 25720; or CSUR P135), or a sequence having more than 85%, preferably more than 90% of identity, notably having 90, 91, 92, 93, 94, 95, 96, 97, 98 or 99% of identity, with SEQ ID NO. 12. This microorganism comprises the gene coding for a TMA methyltransferase having the sequence SEQ ID NO: 2, or an equivalent sequence as defined supra, and the gene coding for a corrinoid protein accepting a methyl group from TMA, having the sequence SEQ ID NO: 6, or an equivalent sequence as defined supra. This microorganism comprises the gene coding for a TMA methyltransferase, this gene having the sequence SEQ ID NO: 4, or an equivalent sequence as defined supra, and the gene coding for a corrinoid protein accepting a methyl group from TMA, this gene having the sequence SEQ ID NO: 8, or an equivalent sequence as defined supra. In an embodiment, the composition comprises the strain Methanomassiliicoccus luminyensis DSM No. 25720, available at the DSMZ collection (Inhoffenstraße 7B, 38124 Braunschweig (Brunswick), Germany).

An alternative means for reduction in situ of TMA is the use of genetically modified organisms, in particular recombinant bacteria. In order to be effective, these bacteria should both express a gene coding for the protein MttB (allowing demethylation of TMA) and for the protein MttC (corrinoid protein, accepting a methyl group taken from TMA by MttB). The expression of an active MttB protein requires that the latter have pyrrolysine in its inside. For this purpose, the recombinant organism should also be (i) capable of synthesizing pyrrolysine and (ii) of incorporating this amino acid during translation of the recombinant protein MttB, which may be achieved by incorporating a dedicated cassette for expanding the genetic code. Thus, the genetically modified organism contains:

- The gene or portion of the gene mttC (for example SEQ ID NO: 7 or 8) coding for a corrinoid protein (for example SEQ ID NO:5 or 6).
- The gene or portion of the gene mttB (for example SEQ ID NO: 3 or 4), coding for the MttB protein (for example SEQ ID NO: 1 or 2). This gene or gene portion present in its coding portion has an intermediate interruption of the reading frame by a stop codon (ideally a UGA (amber) codon as exhibited by the natural case described here in strains 1 and 2 (Methanomassiliicoccus luminyensis and "Ca. methanomethylophilus alvus")
- The genes allow synthesis of pyrrolysine: these genes are borne by the operon pyl, and more particularly relate to the genes pylB, pylC and pylD (mentioned as pylBCD) respectively coding for a lysine mutase/proline-2 methylase, a pyrrolysine synthetase and a proline reductase/pyrrolysine synthase. These coded enzymes allow synthesis of pyrrolysine from two lysines.
- The gene coding for a transfer RNA suppressor of the stop codon used (ideally, a tRNA suppressor of the UGA amber codon, i.e. a tRNA having the anticodon TCA). Ideally, this gene is that of one of the described microorganisms (Methanomassiliicoccus luminyensis and "Ca. Methanomethylophilus alvus"), designated as pylT.
- The gene coding for an amino-acyl tRNA synthetase, allowing grafting of the proper amino acid on the corresponding tRNA: in this case, a pyrrolysine tRNA synthetase has to be used, coded by the gene pylS.

As a microorganism, it is possible to use Escherichia coli. The recombinant E. coli strain comprises the genes mttB, mttC, pylBCD, pylT and pylS. The strain thus expresses the proteins required for synthesizing pyrrolysine. This pyrrolysine is grafted to a specific tRNA (Pyl amber tRNA, coded by pylT) by the action of pyrrolysine-tRNA synthetase. An example of this type of modified organism was moreover described (Longstaff et al, 2007, PNAS 104 (3), pp 1021-1026: "a natural genetic code expansion cassette enables transmissible biosynthesis and genetic encoding of pyrrolysine"; Namy et al., 2007, FEBS letters 581 (27), pp 5285-

5288: "Adding pyrrolysine to the *Escherichia coli* genetic code") and such a strain is viable: it incorporates a pyrrolysine in these proteins as soon as the mRNA contains an amber stop codon in the reading phase.)

This recombinant *E. coli* also expresses the gene mttB, interrupted inside it by an amber stop codon in the reading phase (case of *Archean* genes mttB). This codon is thus recognized by such a recombinant strain as a amber-Pyl codon and gives the possibility of obtaining a protein containing inside it a pyrrolysine, which is enzymatically active. This method mimics what is naturally achieved by methylotrophic methanogenic microorganisms such as for example Methanosarcinales. Further, this method proved to be effective for the gene mtmB1 of *Methanosarcina acetivorans*, containing an internal amber codon, coding for pyrrolysine: The protein coded by mtmB1 (monomethylamine methyltransferase), expressed in an *E. coli* strain expressing pylBCD, pylS, and pylT then contains a pyrrolysine (Longstaff et al, op. cit.; Namy et al, op. cit.). This method may be used in the same way for MttB. The latter, synthesized in a form containing pyrrolysine, may then demethylate TMA into dimethylamine (DMA), by transferring this methyl to an acceptor protein (a corrinoid protein coded by mttC), thereby reducing the TMA concentration.

As another microorganism, it is possible to use a *Lactobacillus*. *Lactobacillus* strains may be used according to the same principles as described for *E. coli*, by using vectors and techniques for bacterial transformation specific to these Gram-positive bacteria (see for example Berthier et al., 1996, Microbiology, 142, pp 1273-1279 or Alegre et al., 2006, FEMS Microbiology Letters, 241 (1), pp 73-77). In this framework, one has a genetically modified organism directly derived from natural commensal hosts of the human intestine and of the vagina, and for some of them, they may also exhibit probiotic initial activities.

In an embodiment, the natural or recombinant microorganisms of the invention are live microorganisms.

In other embodiments, they may be killed or inactivated.

The compositions according to the invention may further comprise a pharmaceutically acceptable carrier or excipient.

In an embodiment, the composition is a culture extract, preferably a concentrated extract. Notably, a concentrated extract of a live microorganism is used.

In an embodiment, the composition or an extract used as an active ingredient in the composition comprises a population of microorganisms essentially consisting or exclusively consisting in methanogenic microorganisms according to the invention. The composition may comprise one species or one single strain of them, or else comprise at least two different species or strains of them.

In another embodiment, the composition or an extract used as an active ingredient in the composition comprises a population of microorganisms comprising at least one species or one strain of a methanogenic microorganism according to the invention, and one or several other microorganisms, notably stemming from cultivation. The composition may comprise a species or a single strain of a methanogenic microorganism according to the invention, or else comprise at least two different species or strains of them.

In an embodiment, the microorganisms are freeze-dried. Freeze-drying is achieved by a standard technique. The composition may then comprise an excipient and/or a standard freeze-drying stabilizer, or any other useful additive.

The invention also relates to another alternative means for trapping and reducing the TMA concentration at the desired sites, based on delivery in situ of at least the active enzyme MttB and of the protein accepting a methyl group MttC. This may be based on two distinct principles:

On the one hand, the purification of these proteins from microorganisms naturally producing MttB and MttC, such as for example the methanogenic Archaea of the order of Methanosarcinales or methanogens related with Thermoplasmatales, such as M. luminyensis or Ca. M. alvus, which may be cultivated in vitro. These may also be other microorganisms of the bacterial type naturally coding for pyrrolysine, a MttB containing a pyrrolysine and an MttC, which may be cultivated in vitro: for example, the bacteria *Acetohalobium arabaticum, Desulfitobacterium hafniense, D. dehalogenans* or *Bilophila wadsworthia*. A list of these microorganisms known to this day is referenced by Prat et al., 2012, PNAS, 109 (51), pp 1070-1075 and additional documents appended to this publication.

On the other hand, the purification of these proteins from recombinant microorganisms. This production/purification may also be facilitated by using systems for producing and secreting heterologous proteins. This may then be carried out in a microorganism such as those described above (*E. coli* or *Lactobacillus*), so as to have a joint production of pyrrolysine, systems allowing its incorporation at amber codons and the expression of a protein MttB containing a pyrrolysine. Moreover, the production of the protein MttC may be carried out in parallel in another organism.

A combined solution of the two, in order to obtain an active MttB protein containing pyrrolysine on the one hand, and the corrinoid protein MttC on the other hand.

The invention therefore relates to a composition comprising a TMA methyltransferase, notably a MttB protein, preferably an MttB protein having the sequence SEQ ID NO: 1 or 2 or an equivalent sequence (of a methyltransferase active on TMA) having more than 90% of identity, notably having 90, 91, 92, 93, 94, 95, 96, 97, 98 or 99% of identity, with SEQ ID NO: 1 or 2.

The invention also relates to a corrinoid protein accepting a methyl group from TMA, having the sequence SEQ ID NO: 5 or 6, or an equivalent sequence (of a corrinoid protein accepting a methyl group capable of capturing the methyls of TMA in the presence of a methyltransferase) having more than 90% of identity, notably having 90, 91, 92, 93, 94, 95, 96, 97, 98 or 99% of identity, with SEQ ID NO: 5 or 6.

Alternatively, the same composition comprises both of these proteins.

Still alternatively, the composition is in the form of a kit comprising both compositions, for separate, simultaneous or sequential administration.

The obtained proteins may therefore be associated with an adequate galenic system allowing, depending on the selected target, intestinal delivery (vectors allowing for gastro-resistance), rectal or vaginal delivery. Delivered in situ, the active MttB protein allows conversion of the TMA into DMA by demethylation of a group, this methyl group may then be transferred to the MttC protein. This regenerates the MttB protein for another demethylation of TMA and results in the reduction of the amount of TMA.

The compositions of the invention also appear in a form adapted to the cavity or organ to be treated. They comprise a suitable carrier or excipient and/or are associated with or included in a galenic form adapted to the administration route.

In an embodiment, the composition preferably appears as an administration form via an oral route.

For the intestine notably, this oral form may advantageously comprise an enteric administration form, notably an enteric capsule, an enteric gelatin capsule, a tablet including an enteric coating, an encapsulation, for example microencapsulation, with a material providing enteric protection, the combination of at least two of these means for which at least one provides enteric protection, etc. The term of enteric means that the administration form protects the composition until it attains the intestine. For example, the composition, notably the lyophilisate of microorganisms, may be coated with a coating by means of protective agents, notably selected as usual from proteins, polysaccharides, gums and other enteric coating agents. In an embodiment, a double coating is achieved according to the teaching of EP 1 514 553.

The administration form may also be adapted to direct administration in a cavity of the body such as the vagina, for example in the form of ovules.

The administration form may also be adapted to administration via a rectal route, for example as a suppository or the like.

In this embodiment, the compositions according to the invention contain from 10 to $10^{13}$ microorganisms.

The object of the present invention is also a treatment method intended to reduce the TMA level in a patient in need thereof.

The object of the invention is therefore a method for reducing or suppressing TMA at a cavity or at a human organ, notably at the intestine, vagina level and/or in the liver, comprising the administration to a patient in need thereof, of a sufficient amount of a composition according to the invention, containing a microorganism expressing a TMA methyltransferase or such an enzyme. This microorganism, by expression of the enzyme or the directly administered enzyme is capable of metabolizing trimethylamine (TMA) in the presence of hydrogen in the cavity, notably the intestine or the vagina. Preferably, the microorganism also expresses a corrinoid protein accepting a methyl group from TMA, or further this protein is also administered. Still preferably, the microorganism also expresses a hydrolase of biliary salts, notably a choloylglycine hydrolase. In an embodiment, the composition comprises a methanogenic Archaea, notably Methanomethylophilus alvus or Methanomassiliicoccus luminyensis.

In a first embodiment, the invention relates to a method for treating trimethylaminuria. The treated patient has a deficiency in the capability of metabolizing TMA. Notably, he/she is deficient in an active FMO3 enzyme.

In a second embodiment, the invention relates to a method allowing reduction in the level of the hepatic metabolite of TMA, TMAO, notably plasma TMAO. This method may aim at preventing the formation of atheromatous plaques and/or preventing cardiovascular diseases. The targeted patient is either a patient capable of metabolizing TMA, or a TMA-metabolism deficient patient but treated with a drug allowing reestablishment of metabolism of TMA into TMAO, for example with the composition according to the invention. Metabolization of the TMA upstream then allows limitation of the TMAO production by the liver.

The method applied in a TMA-metabolism deficient patient allows a combination of both effects, metabolism of TMA or treatment of trimethylaminuria, and reduction of plasma TMAO, prevention of the formation of atheromatous plaques and/or prevention of cardiovascular diseases.

In a third embodiment, the invention relates to a method for treating vaginal fluids in the case of bacterial vaginosis. The method notably aims at reducing or suppressing TMA and/or the smells associated with the presence of TMA.

In a preferred embodiment, the microorganisms are live microorganisms.

In an embodiment, at least one dose containing a sufficient amount of microorganisms or of enzyme in order to obtain the sought effect from between reduction of the TMA level, reduction of the TMAO level or further a combination of both, is administered to the patient. Additional doses may be administered spread out in time, notably at regular time intervals, for example at each meal, in order to maintain the sought effect.

In another embodiment in which the microorganism is necessarily live, either at least one dose immediately efficient for obtaining the sought effect from between reduction of the TMA level, reduction of the TMAO level, or further a combination of both, or a sowing dose, is administered to the patient, the intraintestinal or intravaginal development of the microorganism then giving the possibility of obtaining the sought effect.

In an embodiment, the microorganism is implanted into the intestine in the long run. It is then possible to contemplate one or several (e.g. from one to five) initial doses, for example taken during meals, and then supplements at regular time intervals, or after episodes of intestinal disorder (diarrhoeas or other disorders).

In another embodiment, the microorganism is implanted in the vagina in the long run. It is then possible to contemplate one or several (e.g. from one to five) initial doses, for example taken upon waking up and/or going to sleep, and then supplements at regular time intervals, or after episodes of significant fragrant vaginal losses.

In an embodiment, the administration of microorganisms according to the invention and of the enzyme and/or of the acceptor protein are associated.

The compositions used in these treatment methods may have different developed characteristics supra.

The object of the present invention is also a culture containing a methanogenic Archaea for which the RNA 16S is coded by the DNA sequence SEQ ID NO: 11 (strain 1 identified by the inventors) or a sequence having more than 90% of identity, notably having 90, 91, 92, 93, 94, 95, 96, 97, 98 or 99% of identity, with SEQ ID NO: 11. This microorganism comprises the gene coding for a TMA methyltransferase having the sequence SEQ ID NO: 1, or an equivalent sequence as defined supra, the gene coding for a corrinoid protein accepting a methyl group from TMA, having the sequence SEQ ID NO: 5, or an equivalent sequence as defined supra, and the gene coding for a choloylglycine hydrolase, having the sequence SEQ ID NO: 9, or an equivalent sequence as defined supra. This microorganism comprises the gene coding for a TMA methyltransferase, this gene having the sequence SEQ ID NO: 3, or an equivalent sequence as defined supra, the gene coding for a corrinoid protein accepting a methyl group from TMA, this gene having the sequence SEQ ID NO: 7, or an equivalent sequence as defined supra, and the gene coding for a choloylglycine hydrolase, this gene having the sequence SEQ ID NO: 10, or an equivalent sequence as defined supra. The genome of this strain, designated here as Methanomethylophilus alvus, is shown in SEQ ID NO: 13.

The culture may correspond to a consortium of microorganisms, for example stemming from cultivation of stools of a human patient or of an animal, inter alia containing Methanomethylophilus alvus, and preferably this microorganism represents more than 10%, preferably more than 20, 30, 40, 50, 60, 70, 80, 90% of the microorganisms in the consortium. Notably, this microorganism represents in the consortium, more than 10%, preferably more than 20, 30, 40, 50, 60, 70, 80, 90% of the methanogenic strains the most frequently encountered in humans (Methanobacteriales of the *Methanobrevibacter smithii* and *Methanosphaera stadtmanae* type).

The culture may also be a pure culture of Methanomethylophilus alvus.

The culture comprises a suitable carrier. The culture is maintained under anaerobic conditions.

List of sequences:

| SEQ ID NO: | Amino acids | Nucleotides |
|---|---|---|
| 1 | TMA methyltransferase strain 1 | |
| 2 | TMA methyltransferase strain 2 | |

| SEQ ID NO: | Amino acids | Nucleotides |
|---|---|---|
| 3 | | mttB gene coding for TMA methyltransferase strain 1 |
| 4 | | mttB gene coding for TMA methyltransferase strain 2 |
| 5 | Corrinoid protein accepting a methyl group from TMA strain 1 | |
| 6 | Corrinoid protein accepting a methyl group from TMA strain 2 | |
| 7 | | mttC gene coding for the corrinoid protein accepting a methyl group from TMA strain 1 |
| 8 | | mttC gene coding for the corrinoid protein accepting a methyl group from TMA strain 2 |
| 9 | Hydrolase of biliary salt strain 1 | |
| 10 | | Gene coding for hydrolase of biliary salts strain 1 |
| 11 | | DNA coding for the RNA 16S strain 1 |
| 12 | | DNA coding for the RNA 16S strain 2 |
| 13 | | Genome of strain 1 |
| 14 | | mttb Fw primer |
| 15 | | mttb Rv primer |
| 16-21 | | Primers |

The invention will now be described in more detail by means of non-limiting application examples.

EXAMPLE 1

Method for Isolating and Cultivating a Methanogenic Archaea Consuming TMA 1.1. Molecular Detection Method:

Molecular biology methods give the possibility of detecting and distinguishing methanogenic Archaea consuming TMA (called here Methanomethylophilales) between them. A first phase may consist of detecting methanogenic Archaea by means of the RNA 16S by taking the RNAs 16S of the strains 1 and 2 described supra, or DNAs coding for these RNAs 16S, by means of suitable primers. A second phase (or first phase if the classification has already been achieved) consists of detecting the presence of an mttb (or mttB) gene, and optionally further a mttc (or mttC) gene. Primers which may be used for detecting the mttb gene are the following:

```
Fw: SEQ ID NO: 14:    GCACTTCCACCACATCG

Rv: SEQ ID NO: 15:    AGCTGRGACAGRACGAT
``` wherein R corresponds to a puric base, A or G
Amplicon: 270-300 bp.

1.2. Cultivation, Enrichment and Isolation Method

Cultivation/isolation is initially achieved from fresh stools, from a human: this human may be a person in which the presence of methanogens in general and of Methanomethylophilales in particular will have been detected with molecular detection techniques mentioned above (from DNAs extracted from these stools, according to standard methodologies with the QIAGen DNA Stool Kit). Alternatively, the detection of the presence of Methanomethylophilales may be achieved in parallel with the cultivation, according to the same methodology.

All the manipulations are performed under sterile and strictly anaerobic conditions ($N_2$ flow). The stools, once recovered are immediately treated. Otherwise, alternatively, their preservation may be achieved before use, for several hours at 4° C., in a closed jar, in which anaerobic conditions have been initiated, without any apparent dramatic modification on the results and the survival of the methanogens in the sample.

About 500 to 600 mg of stools are recovered by means of a 1 ml insulin syringe, the end of which is cut (i.e. about 0.4 ml). They are placed in 10 ml of the medium 141 DSMZ (methanogenium medium) specific for methanogenic microorganisms, in a $H_2/CO_2$ atmosphere (80/20, pressure of 2 atm) or in an $N_2$ atmosphere (initially 100%, pressure of 2 atm) in an antibiotic vial of 60 ml.

In order to promote development of Methanomethylophilales, and thus enrich the culture in the consortium, in the tube are further put:

a specific substrate of this group=methanol (final 80 mM), or alternatively, one of its natural <<sources>> in the human colon, i.e. pectin which will be hydrolyzed by other microbes of the consortium (and potentially Methanomethylophilales) so as to obtain methanol inter alia.

Various antibiotics such as bacitracin or metronidazole, (100 mg/l); Dridi et al. (supra) have proposed various antibiotics to which Methanomassiliicoccus luminyensis is resistant (bacitracin, metronidazole, ordinazole, squalamine).

This cultivation is then carried out at 37° C. with slight stirring, the tracking of the cultivation is continuously ensured by quantitative PCR, preferably daily. Depending on the types of strains of Methanomethylophilales, various duplication times are observed, and may vary by one to three times, or even more. As an example, the scenario encountered with stools of a patient bearing Methanomethylophilus alvus is illustrated, from the inoculation of a stool sample. This is a patient having $10^6$ as a number of copies of 16S rRNA genes/ml of *Methanobrevibacter smithii* (Mbs) culture, 10 times more than M. alvus (Mx), and even 10 times more bacteria (stools at the beginning of cultivation, time 0). During the first days of a culture in a standard medium, without providing pectin or methanol, the Mbs and certain bacteria develop much faster and supplant Mx, before stabilization and retarded development of Mx, at levels approaching the initial amount in the sample. This level may be improved by adding methanol, or even pectin, a substrate generating methanol, like in the case at day 20: a sharp improvement in the proportion of Mx is then observed over time relatively to the bacteria and to Mbs. This method may be repeated: during the monitoring (preferably daily monitoring), it is then possible to determine the best time for transplanting the consortium or simply re-supplementing the culture with methanol/pectin (for example on a plateau phase observed from day 20). After a certain number of enrichment cycles, it is possible to achieve isolations of an Mx strain from this mixture, by individualized cultivations of a clone of this liquid medium in consortium. This is carried out by the method of roll-tubes, a method which under anaerobic conditions gives the possibility of obtaining isolated colonies in a DSMZ 141+agar solid medium, in the presence of methanol (anaerobic atmosphere, containing at least $H_2$). In this solid medium culture, the first colonies which appear (1$^{st}$ week) are not the sought Mx. The small colonies which appear subsequently (notably after 2 or 3 weeks of cultivation), are recovered and are used for inoculating individually, colony by colony, tubes with DSMZ-141 medium. In parallel, by quantitative PCR, it is determined whether the transplanted colony is an Mx or not. In the positive case, the isolation is then achieved, the culture is transplanted according to the Mx growth rate in a liquid medium 141 supplemented with methanol, under a H$_2$/CO$_2$ atmosphere. The purity of the isolated strain may then be checked, either by reproducing a second time the method described above (isolated colonies in a solid medium according to the technique of roll-tubes), or by analyzing the dissociation curves obtained on amplicons of quantitative PCRs, or further by sequencing the amplicon 16S.

1.3. Procedure for Fast Quantification of Cultivated Procaryotic Lines

This procedure is used for following in parallel Methanomethylophilales or Mmp (Mx=M. alvus, M. luminyensis, other species), Methanobacteriales (Mbac, such as *Methanobrevibacter smithii* or *Methanosphaera stadtmanae*) and total bacteria (Bac) in enrichment cultures in order to define the best conditions for the growth of M. alvus.

Principle:

Lysis of a small culture aliquot (0.1 to 0.2 ml) at a high temperature+osmotic shock.

Reduction of the concentration of PCR inhibitors by centrifugation and dilution of the supernatant.

Quantification of the groups of interest in qPCR

The quantification calibration ranges are prepared beforehand and consist in PCR amplicons, made with the primers described, purified and quantified according to standard methods.

Equipment:
Centrifuge (set to 4° C.)
Thermomixer (set to 99° C.)
Thermocycler
Mmp, Mbac and Bac primers:

```
MxF (AS-05_Fw; 77):
ggg gTA ggg gTA AAA TCC TG      (SEQ ID NO: 16)

MxR (AS-06_Rv; 78):
Cgg ggT ATC TAA TCC CgT TT      (SEQ ID NO: 17)

MbacF (MbS-01_Fw; 75):
gCg AAC Cgg ATT AgA TAC CC      (SEQ ID NO: 18)

MbacR (MbS-02_Rv; 76):
AgT CTT gCg ACC gTA CTT CC      (SEQ ID NO: 19)

BacF (ES-06_Fw; 71):
ACT CCT ACg ggA ggC Ag          (SEQ ID NO: 20)

BacR (ES-07_Rv; 72):
gTA TTA CCg Cgg CTg CTg         (SEQ ID NO: 21)
```

Note: The MxF and MxR primers both target the Methanomethylophilales close to M. alvus and those close to M. luminyensis. It is possible to determine which of these lines controls the other (or whether there is codominance), in a qualitative way, by observing dissociation curves: the amplicons of M. alvus dissociate around 84° C. while those of M. luminyensis dissociate around 85.5° C. This dissociation temperature difference has never been clearly defined for Methanobacteriales.

Composition of the Mix:
Use of the Eurogentec MESA GREEN qPCR Master Mix kit

| Mix | Volume (µl) |
| --- | --- |
| Final volume | 18 |
| Master Mix | 9 |
| Primer F | 0.8 |
| Primer R | 0.8 |
| H$_2$O | 5.4 |
| gDNA | 2 |

Condition of the qPCR with the Primers Above:
First segment:
95° C. for 10 min
Second segment:
95° C. for 30 s
59° C. for 20 s
72° C. for 30 s
80° C. for 20 s→readout of fluorescence
Third segment (dissociation curve, defined by the apparatus):
95° C. for 1 min
59° C. for 30 s
95° C. for 30 s Note: the readout is performed at 80° C. so that the aspecific double strand DNA is denatured (around 76° C.) before the readout.

DNA Extraction with Heat and Preparation of the Quantification by qPCR

Transfer a little more than 100 µl of culture (with a 1 ml syringe of the 23G type, crossing the septum of the anaerobic culture tube) into an Eppendorf tube Retransfer 100 µl of this sample (with a P100) into another tube Centrifuge at 16,000 g; 4° C.; 10 min; this allows sedimentation of the cells, and gets rid of inhibitors present in the culture medium.

During centrifugation, put 90 µl of milliQ water in 1.5 ml Eppendorfs

Replace the supernatant with 100 µl of distilled H$_2$O; this gives the possibility of removing the free DNAs from dead cells, PCR inhibitors, and generation of an osmotic shock which facilitates lysis.

Add a spatula touch of glass beads of 0.2 µm, and vortex for 5 s

Place in the Thermomixer; at 99° C. without stirring for 3 min, with stirring at 1,400 rpm for 7 min, without stirring for 10 min; the cells are lyzed by the heat Prepare the PCR mix by mixing the water and the primers.

Centrifuge at 16,000 g; 4° C.; 10 min; the cell debris are sedimented and the dissolved content of the cells, including DNA, remains in the supernatant.

Add the master mix into the PCR mix, and begin to spread it out on the plate.

Pick up again 10 µl of supernatant in a clean tube and add it to the 90 µl of milliQ water;

Place the tubes in ice until quantification.

From the qPCR apparatus, on the computer, start the MxPro software package and select «Sybr assay with dissociation curve» in order to allow preheating of the lamp during the dissolution of the gDNAs on the PCR plate.

Distribute the gDNA samples on the plate.

Check that all the wells are well closed.

Centrifuge the plate at a max of 500 g for 5 s in order to make the mixes fall to the bottom of the wells.

Re-enter the PCR program and the plate plan into the software package.

EXAMPLE 2

Preparation of a Composition

The final culture obtained in Example 1.1, containing the methanogenic microorganism of the invention is used for preparing an administrable composition. However, it is preferably usable as a stock, for carrying out cultivations under anaerobic conditions and in the presence of hydrogen and of a substrate containing methanol, propagating the microorganism and preparing batches for making the composition according to the invention. The medium and the cultivation conditions are then those as described earlier (DSM 141 medium, supplemented with methanol, under an anaerobic atmosphere containing $H_2$). The obtained cultures are optionally concentrated and are freeze-dried, before being incorporated into enteric gelatin capsules.

EXAMPLE 3

Preparation of a Composition

A culture of the DSM No. 25720 strain is produced, and the cultures are used for preparing batches for making the composition according to the invention. The cultures are made under anaerobic conditions and in the presence of hydrogen and of a substrate containing methanol (for example, DSM 141 medium, supplemented with methanol, under an anaerobic atmosphere containing $H_2$). The obtained cultures are optionally concentrated and are freeze-dried, before being incorporated into enteric gelatin capsules.

EXAMPLE 4

Preparation of a Composition

A culture of the DSM No. 25720 strain is produced, and the cultures are used for preparing batches for making the composition according to the invention. The cultures are made under anaerobic conditions and in the presence of hydrogen and of a substrate containing methanol (for example, DSM 141 medium, supplemented with methanol, under an anaerobic atmosphere containing $H_2$). The obtained cultures are optionally concentrated and are freeze-dried, before being incorporated into vaginal suppositories. These vaginal suppositories are administration forms suitable for being placed in the vagina.

EXAMPLE 5

Pure Culture of Methanomassiliicoccus Luminyensis in the Absence or in the Presence of TMA Composition of the Culture Medium Before preparing the composition of the culture medium, three aqueous solutions comprised in the composition of the culture medium are prepared. These three solutions are an aqueous solution of vitamins, an aqueous solution of trace elements and an aqueous solution of fatty acids.

Composition of the Aqueous Solution of Trace Elements:

TABLE 1

| Composition of the aqueous solution of trace elements | |
|---|---|
| Distilled water | 1000 ml |
| Nitriloacetic acid | 1.5 g |
| Magnesium sulfate hydrate ($MnSO_4 \cdot H_2O$) | 0.5 g |
| Iron sulfate heptahydrate ($FeSO_4 \cdot 7H_2O$) | 100 mg |
| Cobalt sulfate heptahydrate ($CoSO_4 \cdot 7H_2O$) | 180 mg |
| Zinc sulfate heptahydrate ($ZnSO_4 \cdot 7H_2O$) | 180 mg |
| Copper sulfate pentahydrate ($CuSO_4 \cdot 5H_2O$) | 10 mg |
| Aluminium and potassium sulfate dodecahydrate ($KAl(SO_4)_2 \cdot 12H_2O$) | 20 mg |
| Boric acid ($H_3BO_3$) | 10 mg |
| Sodium molybdate dihydrate ($Na_2MoO_4 \cdot 2H_2O$) | 10 mg |
| Nickel chloride hexahydrate ($NiCl_2 \cdot 6H_2O$) | 30 mg |
| Sodium selenite ($Na_2SeO_3 \cdot 5H_2O$) | 30 mg |

The aqueous solution of trace elements is prepared by mixing the compounds with the proportions indicated in table 1 in 1,000 ml of distilled water at room temperature and at atmospheric pressure.

Composition of the Aqueous Solution of Vitamins:

TABLE 2

| Composition of the aqueous solution of vitamins | |
|---|---|
| Distilled water | 1000 ml |
| Biotin | 2 mg |
| Folic acid | 2 mg |
| Pyridoxine hydrochloride | 10 mg |
| Thiamine hydrochloride dihydrate | 5 mg |
| Riboflavin | 5 mg |
| Nicotinic acid | 5 mg |
| Pantothenic acid | 5 mg |
| Vitamin B12 | 0.1 mg |
| Aminobenzoic acid (vitamin L) | 5 mg |
| Lipoic acid | 5 mg |

The aqueous solution of vitamins is prepared by mixing the compounds with the proportions indicated in Table 2 in 1,000 ml of distilled water at room temperature and at atmospheric pressure.

Composition of the Aqueous Solution of Fatty Acids:

TABLE 3

| Composition of the aqueous solution of fatty acids | |
|---|---|
| Distilled water | 20 ml |
| Valeric acid | 0.53 ml |
| Isovaleric acid | 0.53 ml |
| 2-methylbutyric acid | 0.53 ml |
| Isobutyric acid | 0.53 ml |

The aqueous solution of fatty acids is prepared by mixing the compounds with the proportions indicated in Table 3 in 1,000 ml of distilled water at room temperature and at atmospheric pressure.

Composition of the Culture Medium:

TABLE 4

| Composition of the culture medium | |
|---|---|
| Distilled water | 1000 ml |
| Magnesium sulfate heptahydrate ($MgSO_4 \cdot 7H_2O$) | 0.4 g |
| Ammonium chloride ($NH_4Cl$) | 0.4 g |
| Calcium chloride dihydrate ($CaCl_2 \cdot 2H_2O$) | 0.05 g |
| Sodium chloride (NaCl) | 0.4 g |
| Potassium dihydrogen phosphate ($KH_2PO_4$) | 0.5 g |
| Aqueous solution of trace elements | 10 ml |
| Aqueous solution of vitamins | 10 ml |
| Aqueous solution of fatty acids | 20 ml |
| Iron sulfate heptahydrate ($FeSO_4 \cdot 7H_2O$) | 2.0 mg |
| Sodium acetate | 1 g |
| Yeast extract | 1 g |
| Sodium formate | 2 g |
| Ruminal liquid | 50 ml |
| Resazurin | 0.7 mg |

Preparation of Tubes Comprising the Composition of the Culture Medium

The composition of the culture medium is brought to the boil for 5 minutes, and is then cooled under a nitrogen-containing atmosphere ($N_2$). When the temperature is below 50° C., 4 g of sodium bicarbonate ($NaHCO_3$) are added per liter of composition of the culture medium. The composition of the thereby obtained culture medium is distributed into anaerobic culture tubes of the "Hungate" or "Balch" type under an $N_2$ atmosphere, and these tubes are then placed in an autoclave for 20 minutes at 120° C.

The composition of the culture medium comprised in the tubes has a pH of 7.4.

Preparation of Pure Cultures of Methanomassiliicoccus Luminyensis (M. Luminyensis)

Three series of tubes having differences in the composition of their gaseous phase, in the presence or in the absence of $H_2$ and in the composition of the culture medium, in the presence or in the absence of trimethylammonium hydrochloride (TMA.HCl), are designated as A, B and C, and are prepared in the following way from tubes comprising the composition of the initial culture medium as described above.

0.1 ml of a sterile solution of sodium sulfide ($Na_2S$) at 15 g/l (0.2 M) is added to the composition of the culture medium comprised in the tubes of the A, B and C series, so that a final concentration of 3.5 mM of $Na_2S$ is obtained in each of the tubes.

An anoxic and sterile aqueous solution of trimethylammonium hydrochloride (TMA-HCl) was also added (0.2 ml at 1 M) in each of the tubes of the A and B series so that a final concentration comprised between 35 and 40 mM of TMA.HCl is obtained in each of the tubes of the A and B series.

The pre-culture of the strain M. luminyensis B10 (DSM25270) is inoculated in an amount of 10% of the volume of the composition of the culture medium comprised in each of the tubes.

The atmosphere of the tubes (initially only containing $N_2$) is modified by adding $CO_2$ in the whole of the tubes of the A, B and C series and by addition of $H_2$ in the whole of the tubes of the A and C series in order to obtain the gas compositions described in Table 5.

TABLE 5

| Compositions of the anaerobic atmosphere | | | |
|---|---|---|---|
| Atmosphere composition (%) | Tube series A | Tube series B | Tube series C |
| $H_2$ | 55 | 0 | 55 |
| $N_2$ | 35 | 85 | 35 |
| $CO_2$ | 10 | 15 | 10 |

The tubes of the A, B and C series are incubated at 37° C., and tracking of the culture of M. luminyensis is performed over time, punctuated by samplings and dosages indicated by a cross according to the program described in Table 6 below.

The conducted measurements for tracking the culture of M. luminyensis in the tubes of the A, B and C series are the measurement of the optical density (O.D.) at a wavelength of 600 nm, the measurement of the remaining trimethylamine concentration in each tube, the measurement of the proportion of dihydrogen ($H_2$) in the gas phase and the measurement of the methane ($CH_4$) proportion in the gas phase.

The measurement of the dihydrogen ($H_2$) proportion is an indicator of $H_2$ consumption during the production of methane ($CH_4$) (from trimethylamine) and the measurement of the methane ($CH_4$) proportion in the gas phase. The measurement of the O.D. gives the possibility of quantifying by turbidimetry the cell growth of M. luminyensis.

The measurement of the amount of trimethylamine by M. luminyensis is conducted according to the method described by Kratzer et al. (2009, Journal of Bacteriology, 191 (16), pp 5108-5115, "Transcriptional Profiling of Methyltransferase Genes during Growth of *Methanosarcina mazei* on Trimethylamine"), with the following modifications:

200 µl of culture are sampled from each tube comprising the culture and placed in a sterile tube, the tube comprising 200 µl of culture is centrifuged at 13,000 g for 10 min, and 50 µl of supernatant are sampled from this tube and again placed in a sterile tube, 783 µl of distilled water and 125 µl of sodium bicarbonate ($NaHCO_3$) at 20% (m/v) are added into the tube comprising 50 µl of supernatant, 42 µl of Fiolin-Ciocalteu reagent are then added, the thereby obtained tube is left for stirring for 60 min, and then the absorbance of the solution comprised in this tube is measured at 745 nm relatively to a calibration range covering a concentration from 0 to 50 mM of TMA made according to the same procedure.

The gas composition of the anaerobic atmosphere in which are placed the tubes of series A, B and C is determined by gas chromatography from a gas volume of 2 mL sampled through the septum.

An average of the values measured for O.D., of the amounts of trimethylamine and of the amounts of $H_2$ in each tube overtime according to the M. luminyensis cultures comprised in each series of tubes is indicated in Table 7 below.

TABLE 6

Program of samplings and dosages over time in order to ensure the tracking of the *M. luminyensis* culture in tubes of the A, B and C series.

| | Time (hours) | | | | | | | | | | |
|---|---|---|---|---|---|---|---|---|---|---|---|
| | 0 | 24 | 48 | 72 | 104 | 149 | 173 | 197 | 247 | 295 | 388 |
| O.D. at 600 nm | X | X | X | X | X | X | X | X | X | X | X |
| TMA dosage | | X | | | | X | | X | | | X |
| Measurement of $CH_4$ | X | | X | | X | | | | | | X |
| Measurement of $H_2$ | X | | X | | X | | | | | | X |

TABLE 7

Averages of the values of O.D., of the amounts of trimethylamine and of the amounts of H$_2$ measured in the tubes of series A, B and C over time for cultures of *M. luminyensis* comprised in each of the series A, B and C of tubes.

| | Sampling time in hours | | | | | | | | | | |
|---|---|---|---|---|---|---|---|---|---|---|---|
| | 0 | 24 | 48 | 72 | 104 | 149 | 173 | 197 | 247 | 295 | 388 |
| Average of the measurements of O.D. for the culture of *M. luminyensis* in tubes of series A | 0 | 0 | 0.01 | 0.03 | 0.05 | 0.08 | 0.10 | 0.12 | 0.14 | 0.16 | 0.19 |
| Average of the measurements of O.D. for the culture of *M. luminyensis* in tubes of series B | 0 | 0 | 0.01 | 0 | 0.01 | 0.01 | 0 | 0 | 0 | 0 | 0 |
| Average of the measurements of O.D. for the culture of *M. luminyensis* in tubes of series C | 0 | 0 | 0 | 0 | 0 | 0 | 0 | 0 | 0 | 0 | 0 |
| Average of the concentration in mM of TMA in the tubes of series A | x | 39.9 | x | x | x | 24.0 | x | 22.6 | x | x | 12.2 |
| Average of the concentration in mM of TMA in the tubes of series B | x | 38.0 | x | x | x | 35.6 | x | 35.7 | x | x | 34.2 |
| Average of the concentration in mM of TMA in the tubes of series C | x | 0 | x | x | x | 0 | x | 0 | x | x | 0 |
| Average of the percentage of CH$_4$ produced by the culture of *M. luminyensis* in tubes of series A | 0.02 | x | x | 2.65 | x | 8.15 | x | x | x | x | 20.49 |
| Average of the percentage of CH$_4$ produced by the culture of *M. luminyensis* in tubes of series B | 0.03 | x | x | 0.04 | x | 0.38 | x | x | x | x | 0.33 |
| Average of the percentage of CH$_4$ produced by the culture of *M. luminyensis* in tubes of series C | 0.03 | x | x | 0.03 | x | 0.04 | x | x | x | x | 0.03 |
| Average of the percentage of H$_2$ in the tubes of series A | 55.42 | x | x | 50.14 | x | 44.02 | x | x | x | x | 30.46 |
| Average of the percentage of H$_2$ in the tubes of series B | 0.10 | x | x | 0.89 | x | 0.71 | x | x | x | x | 0.67 |
| Average of the percentage of H$_2$ in the tubes of series C | 55.10 | x | x | 55.20 | x | 54.20 | x | x | x | x | 55.10 |

A growth of the M. luminyensis culture is observed only in the tubes of series A providing both TMA, which is used by M. luminyensis and decreases over time, and $H_2$. This growth of the M. luminyensis culture requires production of methane ($CH_4$), the content of which increases over time.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10238695B2). An electronic copy of the "Sequence Listing" will also be available from the USPTO upon request and payment of the fee set forth in 37 CFR 1.19(b)(3).

The invention claimed is:

1. A method for reducing or suppressing trimethylamine (TMA) present in a human cavity in a human patient in need thereof, comprising:
   administering an effective amount of a composition containing a methanogenic Archaea expressing a TMA methyltransferase, wherein said expressed TMA methyltransferase is capable of reducing or suppressing TMA in said cavity through metabolizing TMA in the presence of hydrogen in said human cavity, and
   having the methanogenic Archaea delivered into the human cavity which is the intestine which comprises microbial flora able to produce said TMA,
   wherein the methanogenic Archaea when present in the intestine has a TMA metabolism, produces TMA methyltransferase, and metabolizes intestinal TMA in the presence of $H_2$, and
   whereby said TMA present in the intestine is metabolized in the intestine to methane, and TMA is reduced or suppressed in the intestine and in the liver.

2. The method according to claim 1, for treating trimethylaminuria.

3. The method according to claim 1, wherein the method also reduces the plasma trimethylamine-N-oxide (TMAO) produced from said TMA in the liver as a result of TMA reduction or suppression in the intestine and in the liver, wherein TMAO may contribute to the development of atheromatous plaques in the arteries.

4. The method according to claim 1, wherein the methanogenic Archaea also expresses a corrinoid protein accepting a methyl group from TMA.

5. The method according to claim 1, wherein the methanogenic Archaea comprises the gene coding for a TMA methyltransferase of sequence SEQ ID NO: 1 or 2.

6. The method according to claim 1, wherein the methanogenic Archaea comprises the gene coding for a TMA methyltransferase, the gene having the sequence SEQ ID NO: 3 or 4.

7. The method according to claim 1, wherein the methanogenic Archaea also includes a gene for resistance to biliary salts.

8. The method according to claim 1, wherein the RNA 16S of the methanogenic Archaea is coded by the DNA sequence SEQ ID NO: 11 or 12.

9. The method according to claim 7, wherein the gene for resistance to biliary salts is choloylglycine hydrolase.

10. A method for reducing or suppressing trimethylamine (TMA) present in a human cavity in a human patient in need thereof, comprising:
    administering an effective amount of a composition containing a methanogenic Archaea the RNA 16S of which is coded by the DNA sequence SEQ ID NO: 11 or 12, a methanogenic Archaea comprising a gene coding for a TMA methyltransferase of sequence SEQ ID NO: 1 or 2, or a methanogenic Archaea containing a TMA methyltransferase of sequence SEQ ID NO: 1 or 2, wherein said TMA methyltransferase is capable of reducing or suppressing TMA in said cavity through metabolizing TMA in the presence of hydrogen in said human cavity, and
    having the methanogenic Archaea delivered into the human cavity which is the intestine which comprises microbial flora able to produce said TMA, wherein said methanogenic Archaea is a methanogenic Archaea that when present in the intestine has a TMA metabolism, wherein said methanogenic Archaea produces TMA methyltransferase and metabolizes intestinal TMA in the presence of $H_2$, and
    whereby said TMA present in the intestine is metabolized in the intestine to methane and TMA is reduced or suppressed in the intestine and in the liver.

* * * * *